United States Patent
Smits et al.

(10) Patent No.: US 8,530,486 B2
(45) Date of Patent: Sep. 10, 2013

(54) QUINAZOLINES AND RELATED HETEROCYCLIC COMPOUNDS, AND THEIR THERAPEUTIC USE

(75) Inventors: Rogier Adriaan Smits, Amsterdam (NL); Regorius Leurs, Amsterdam (NL); Iwan Jozef Philomena De Esch, Amsterdam (NL)

(73) Assignee: Vereniging Voor Christelijk Hoger Onderwijs, Wetenschappelijk Onderzoek en Patientenzorg, Amsterdam (NL)

( * ) Notice: Subject to any disclaimer, the term of this patent is extended or adjusted under 35 U.S.C. 154(b) by 195 days.

(21) Appl. No.: 12/811,547

(22) PCT Filed: Jan. 2, 2009

(86) PCT No.: PCT/EP2009/050012
§ 371 (c)(1),
(2), (4) Date: Aug. 9, 2010

(87) PCT Pub. No.: WO2009/083608
PCT Pub. Date: Jul. 9, 2009

(65) Prior Publication Data
US 2010/0298322 A1 Nov. 25, 2010

(30) Foreign Application Priority Data
Jan. 2, 2008 (EP) .................................. 08100015

(51) Int. Cl.
*A61K 31/517* (2006.01)
(52) U.S. Cl.
USPC ........................................ 514/266.2; 544/293
(58) Field of Classification Search
USPC ........................................................ 544/293
See application file for complete search history.

(56) References Cited

U.S. PATENT DOCUMENTS

| 3,956,495 A | 5/1976 | Lacefield |
| 5,439,895 A * | 8/1995 | Lee et al. ............ 514/63 |
| 2005/0070527 A1 | 3/2005 | Edwards et al. |

FOREIGN PATENT DOCUMENTS

| DE | 2121031 A1 | 11/1972 |
| EP | 0 579 496 | 1/1994 |
| EP | 1 767 537 | 3/2007 |
| WO | WO 02/072548 | 9/2002 |
| WO | WO 2006/050965 | 5/2006 |
| WO | WO 2009/047255 | 4/2009 |

OTHER PUBLICATIONS

Fujiwara et al. "Synthesis and bioactivities of novel piperidylpyrimidine derivatives: Inhibitors of tumor necrosis factor-alpha production" *Bioorganic & Medicinal Chemistry Letters*, 2000, pp. 1317-1320, vol. 10.
Gineinah etal. "Synthesis and antiinflammatory screening of some quinazoline and quinazolyl-4-oxoquinazoline derivatives" *Arch. Pharm. Pharm. Med. Chem.*, 2002, pp. 556-562, vol. 11.

* cited by examiner

*Primary Examiner* — Brian McDowell
(74) *Attorney, Agent, or Firm* — Saliwanchik, Lloyd & Eisenschenk

(57) ABSTRACT

A compound of the formula (I) wherein X is $CR^1$ or N; Y is $CR^3$ or N; $R^1$, $R^3$, $R^4$, $R^5$ and $R^6$ are independently H, F, Cl, Br, I, or a hydrocarbon group which optionally contains one or more heteroatoms; $R^7$ is a heterocyclic group including one or more N atoms; R' is $R^x$ or $NR^yR^z$ wherein $R^x$, $R^y$ and $R^z$ are each H or the same or different groups, including cyclic groups formed by $R^y$ and $R^z$ with the N atom, of up to 20 C atoms and optionally including up to 3 further heteroatoms selected from N, O and S; or a pharmaceutically acceptable salt, ester or solvate thereof.

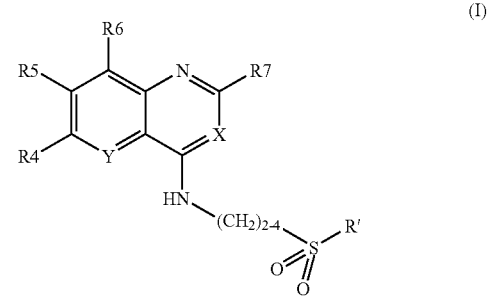

6 Claims, No Drawings

QUINAZOLINES AND RELATED HETEROCYCLIC COMPOUNDS, AND THEIR THERAPEUTIC USE

CROSS REFERENCE TO A RELATED APPLICATION

This application is a National Stage Application of International Application Number PCT/EP2009/050012, filed Jan. 2, 2009; which claims priority to European. Patent Application No. 08100015.0, filed Jan. 2, 2008; which are incorporated herein by reference in their entirety.

FIELD OF THE INVENTION

The present invention relates to quinazolines and related heterocyclic compounds, and their therapeutic use. More particularly, it relates to compounds that interact with a histamine receptor, and their use for treating, reducing or preventing disorders and discomforts mediated by a histamine receptor.

BACKGROUND OF THE INVENTION

Histamine is important in human physiology because it is one of the chemicals released from certain cells (particularly mast cells) upon tissue injury or during the neutralisation of foreign material (e.g. antigens) by certain types of antibodies. Released histamine tends to dilate blood capillaries, often causing the skin to appear red and feel warm, and makes the capillaries more permeable, allowing fluid to escape into the surrounding tissue.

The biological activity of histamine is closely related with allergic responses and its deleterious effects, such as inflammation. Events that induce the inflammatory response include physical stimulation (including trauma), chemical stimulation, infection, and invasion by microorganisms. The inflammatory response is characterised by pain, increased temperature, redness, swelling, reduced function, itch, or any combination of these.

Mast cell degranulation (exocytosis) releases histamine and leads to an inflammatory response. A wide variety of immunological stimuli and non-immunological stimuli may cause the activation, recruitment and degranulation of mast cells. The activation of mast cells initiates allergic inflammatory responses, which in turn cause the recruitment of other effector cells that further contribute to the inflammatory response.

The numerous functions that are exerted by histamine are mediated through at least four pharmacologically distinct receptors, which are all members of the G-protein-coupled receptor family. The $H_1$ receptor is expressed in the brain, endothelial cells, and smooth muscle cells. Many of its functions contribute to allergic responses, and $H_1$ receptor antagonists have been very successful drugs for the treatment of allergies. The $H_2$ receptor has been demonstrated to function as a key modulator for gastric acid secretion, and $H_2$ receptor antagonists are widely used for the treatment of gastrointestinal ulcers. The $H_3$ receptor is predominantly expressed in the human central nervous system. It is believed to function as a presynaptic release-controlling receptor that may regulate histamine, norepinephrine, serotonin, GABA, acetylcholine, and other neurotransmitters. The histamine receptors couple to different signalling pathways via different G-proteins.

Recently, several groups have identified and characterised a fourth histamine receptor (see, e.g., T. Oda et al., *J. Biol. Chem.* 2000, 275 (47), 36781-36786; C. Liu et al., *Mol. Pharmacol.* 2001, 59 (3), 420-426; T. Nguyen et al., *Mol. Pharmacol.* 2001, 59 (3), 427-433; Y. Zhu et al., *Mol. Pharmacol.* 2001, 59 (3), 434-441; K. L. Morse et al., *J. Pharmacol. Exp. Ther.* 2001, 296 (3), 1058-1066). The histamine $H_4$ receptor is a seven-transmembrane, G-protein-coupled receptor with approximately 40% homology to the histamine $H_3$ receptor. However, in contrast to the $H_3$ receptor, the $H_4$ receptor is expressed at greater levels in e.g. mast cells, eosinophils and a variety of other cells of the immune system.

It has been shown that administration of a histamine $H_4$ receptor antagonist inhibits histamine $H_4$ receptor-mediated calcium influx and chemotaxis of mast cells (Thurmond et al., *J. Pharmacol. Exp. Ther.* 2004, 309 (1), 404-413) and eosinophils (Raible et al., *Am. J. Respir. Crit. Care Med.* 1994, 149 (6), 1506-1511). This suggests an important role for the histamine $H_4$ receptor for the treatment of inflammatory diseases such as asthma, inflammatory bowel disease and several dermatological disorders. Further, histamine $H_4$ is associated with cancer and itch. See J. K. Bell et al., *Br. J. Pharmacol.* 2004, 142 (2), 374-380; and F. Cianchi et al., *Clin. Cancer Res.* 2005, 11, 6807-6815.

US2005/0070527 describes 1H-quinoxaline compounds that inhibit leukocyte recruitment and modulate the $H_4$ receptor, and their use in treating conditions such as inflammation.

Further prior art in this general area includes WO2006/050965, WO02/072548, US20050070550A1, WO2007/031529, WO2004/022537, EP1767537A1 and US2006/0111416.

PCT/EP2007/056689 discloses compounds of formula I

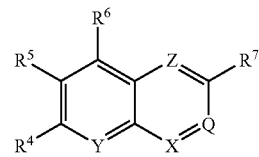

wherein
Q is $CR^1$ or N;
X is $CR^2$ or N, provided that Q and X are not both N;
Y is $CR^3$ or N;
Z is CH or N;
$R^1$, $R^2$, $R^3$, $R^4$, $R^5$ and $R^6$ are independently H, F, Cl, Br, I, or a hydrocarbon group which optionally contains one or more heteroatoms; and
$R^7$ is a heterocyclic group including one or more N atoms;
or a pharmaceutically acceptable salt, ester or solvate thereof.

SUMMARY OF THE INVENTION

According to the present invention, novel compounds are of formula I as defined above but wherein Z is N and X is C—NH—$(CH_2)_{2-4}$—$SO_2R'$ and R' is $R^x$ or $NR^yR^z$ wherein $R^x$, $R^y$ and $R^z$ and each H or the same or different groups having up to 20 C atoms and optionally also heteroatoms.

According to a further aspect of the invention, compounds of the invention can be used to treat, reduce or prevent disorders and discomforts mediated by the histamine $H_4$ receptor. For this purpose, they may be administered to a subject, e.g. as a pharmaceutical composition, in a therapeutically effective amount.

DESCRIPTION OF THE INVENTION

Compounds of the invention may be chiral. This invention includes such compounds in any enantiomeric or diastereomeric form, including racemates. Compounds of the invention may also exist in different tautomeric forms, and atoms in different isomeric forms, and all are included.

Preferably, $R^1$ is selected from H, F, Cl, Br, I, $C_{1-4}$ alkyl, $C_{2-5}$ alkenyl, $C_{1-4}$ alkoxy, cycloalkyl, aryl (such as phenyl), heteroaryl, —$C_{1-4}$ alkyl-aryl such as benzyl or phenethyl, —$C_{1-4}$ alkyl-heteroaryl, such as heteroarylethyl, O-aryl such as O-phenylaryl, O-heteroaryl, NH-aryl such as NH-phenyl, NH-heteroaryl, S-aryl (such as S-phenyl), S-heteroaryl, O—$C_{1-4}$ alkyl-aryl such as O—$CH_2$-phenyl, O—$(CH_2)_2$-phenyl or O—$(CH_2)_4$-phenyl, O—$C_{1-4}$ alkyl-heteroaryl such as O—$(CH_2)_2$-heteroaryl or O—$(CH_2)_4$-heteroaryl, $C_{1-4}$ alkyl-heteroaryl such as $CH_2CH_2$-heteroaryl, NH—$C_{1-4}$ alkyl-aryl such as $NHCH_2$-phenyl, NH—$C_{1-4}$ alkyl-heteroaryl, hydrazino, hydroxylamino, $NH_2$, O—$(CH_2)_3$—N$(CH_3)_2$ and $NR^aR^b$, wherein either $R^a$ is absent and $R^b$ is acyl, or each of $R^a$ and $R^b$ is independently selected from H, $C_{1-4}$ alkyl, cycloalkyl, phenyl, benzyl and phenethyl, wherein any of said aryl, heteroaryl, alkyl, acyl, phenyl and cycloalkyl moieties is optionally substituted with 1 to 3 substituents, e.g. selected from $C_{1-4}$ alkyl, halogen, hydroxyl, amino and $C_{1-3}$ alkoxy.

Preferably, $R^3$, $R^4$, $R^5$ and $R^6$ are independently selected from H, F, Cl, Br, I, $C_{1-4}$ alkyl, $C_{2-5}$ alkenyl, $C_{2-5}$ alkynyl, $C_{1-4}$ alkoxy, $C_{1-4}$ alkylthio, $C_{3-6}$ cycloalkyl, O—$C_{3-6}$ cycloalkyl, phenyl, benzyl, O-phenyl, NH-phenyl, S-phenyl, O—$C_{1-4}$ alkyl-phenyl such as O—$(CH_2)_2$-phenyl or O—$(CH_2)_4$-phenyl, $C_{1-4}$ alkyl-aryl such as $CH_2CH_2$-phenyl, $CF_3$, O—$CF_3$, S—$CF_3$, hydroxy, nitro, cyano, O—$C_{1-4}$ alkyl-N$(CH_3)_2$, O—$(CH_2)_3$—N$(CH_3)_2$ and $NR^aR^b$, wherein each of $R^a$ and $R^b$ is independently selected from H, $C_{1-4}$ alkyl, phenyl, benzyl and phenethyl, and wherein any phenyl, alkyl or cycloalkyl moiety is optionally substituted with 1 to 3 substituents selected from $C_{1-3}$ alkyl, halogen, hydroxy, amino and $C_{1-3}$ alkoxy.

As indicated above, $R^7$ is a heterocyclic group comprising one or more N atoms. It is bonded to the bicyclic nucleus via a N or C atom, bonding via N being preferred. This group may be mono- or bi-cyclic, and optionally carries substituents, e.g. substituents as defined above.

By way of example, $R^7$ is selected from 4-7 membered heterocyclyl, $C_{3-7}$ cycloalkyl-4-7 membered heterocyclyl and bis-(4-7 membered heterocyclyl). In a preferred embodiment, $R^7$ is selected from cyclic amines, spiroamines and bridged cycloamines.

$R^7$ may in particular be selected from any of the following groups (II)

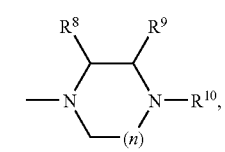

(III)

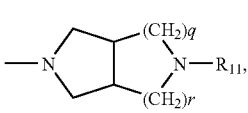

(IV)

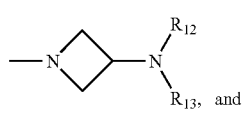

(V)

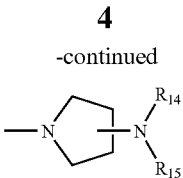

wherein n is 1 or 2;

$R^8$ and $R^9$ are independently H or $C_{1-3}$ alkyl;

$R^{10}$ is H, $C_{3-5}$ alkenyl with no $sp^2$-carbon member attached directly to the $R^{10}$-attached nitrogen member, $C_{3-5}$ alkynyl with no sp-carbon member attached directly to the $R^{10}$-attached nitrogen member, $CH_2CH_2OH$, $C_{1-4}$ alkyl-O—$C_{1-4}$ alkyl or $C_{1-6}$ alkyl which is optionally substituted by halogen, cyano, hydroxy, carboxy, amino, $C_{1-6}$ alkylamino, N,N-di($C_{1-6}$ alkyl)amino, $C_{1-6}$ alkylthio, $C_{1-6}$ alkoxy or $C_{3-8}$ cycloalkyl;

alternatively $R^{10}$ may be taken together with $R^9$, wherein the $R^9$-attached carbon member, and the $R^{10}$-attached nitrogen member form a 5-, 6-, or 7-membered heterocyclic ring, wherein said ring has 0 or 1 additional heteroatoms selected from O, S, NH and N$C_{1-6}$ alkyl, and wherein said heterocyclic ring is substituted with 0, 1, 2 or 3 substituents each selected from $C_{1-3}$ alkyl, halogen, hydroxy, amino and $C_{1-3}$ alkoxy;

q is 1, 2 or 3;

r is 0 or 1;

$R^{11}$ is a hydrogen atom or $C_{1-6}$ alkyl optionally substituted by halogen, cyano, hydroxy, carboxy, amino, N—($C_{1-6}$ alkyl)amino, N,N-di($C_{1-6}$ alkyl)amino, $C_{1-6}$ alkylthio, $C_{1-6}$ alkoxy, or $C_{3-8}$ cycloalkyl; and $R^{12}$, $R^{13}$, $R^{14}$ and $R^{15}$ are independently hydrogen or $C_{1-6}$ alkyl optionally substituted by halogen, cyano, hydroxy, carboxy, amino, $C_{1-6}$ alkylamino, N—($C_{1-6}$ alkyl)amino, N,N-di($C_{1-6}$ alkyl)amino, $C_{1-6}$ alkylthio, $C_{1-6}$ alkoxy, or $C_{3-8}$ cycloalkyl.

The following aminergic substituents are examples of $R^7$:

1

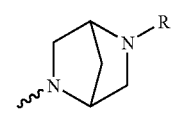

2

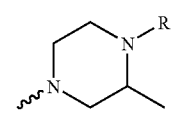

3

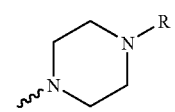

4

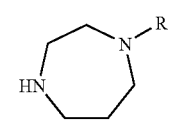

5

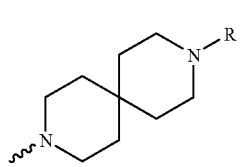

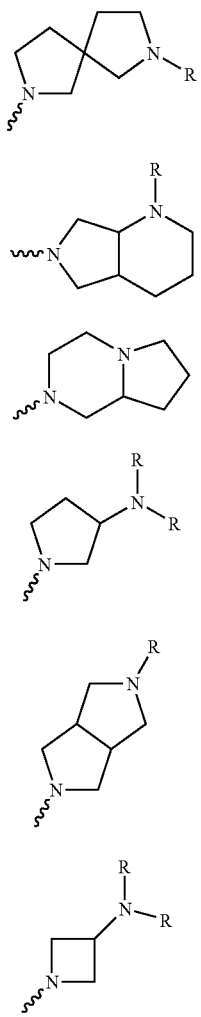

wherein R is H or any substituent, e.g. methyl or ethyl, and the curved lines represent the bond of the amine group with the heterocyclic scaffold. Amines 5 and 6 are examples of spiroamines. Amines 7, 8, 9 and 10 are examples of compounds that have stereoisomers, of which all forms (e.g. S- and R-isomers) are included.

As indicated above, $R^7$ may also be linked to the bicyclic nucleus via a C atom. Examples of such groups are 7-octahydroindolizinyl and 1-methyl-4-piperidinyl.

The broad nature of the group $R^7$ is illustrated in the prior art documents identified above. The content of each is incorporated herein by reference.

$R^x$, $R^y$ and $R^z$ may each be any of the groups defined above. These include alkyl, cycloalkyl, aryl, heterocyclyl and also heterocyclic rings defined by $NR^yR^z$. Each may be substituted.

Typically, a heterocyclic group contains up to 6, 10 or 20 C atoms and up to 3 heteroatoms selected from N, O and S. The group may comprise one ring or fused rings, and may be saturated or partially or wholly unsaturated.

The term "alkyl" as used herein includes straight-chain and branched hydrocarbon groups.

The term "alkenyl" as used herein includes straight-chain and branched hydrocarbon groups as above with at least one carbon-carbon double bond ($sp^2$).

The term "alkynyl" as used herein includes straight-chain and branched hydrocarbon groups as above with at least one carbon-carbon triple bond (sp). Hydrocarbons having a mixture of double bonds and triple bonds are grouped as alkynyls herein.

The term "alkoxy" as used herein includes straight-chain and branched alkyl groups with a terminal oxygen linking the alkyl group to the rest of the molecule.

The term "aryl" as used herein includes any functional group or substituent comprising an aromatic ring. In particular the aryl may be selected from moieties comprising a phenyl, naphtyl or biphenyl. The aryl may comprise one or more heteroatoms, in which case the aryl may be referred to as "heteroaryl". Preferred examples of heteroaryl groups include pyridine, furane, thiophene, triazole and tetrazole.

Any hydrocarbon group may be, for example, a $C_{1-20}$ hydrocarbon, preferably a $C_{1-12}$ hydrocarbon, and more preferably a $C_{1-10}$ hydrocarbon. This range applies also to other groups, including heterocyclic groups, and also as a preference.

It is understood that substitutions and combinations of substitutions recited herein refer to substitutions that are consistent with the valency of the member being substituted.

The "pharmaceutically acceptable salt, ester or solvate thereof" refers to those salts, ester forms and solvates of the compounds of the present invention that would be apparent to the pharmaceutical chemist, i.e. those that are non-toxic and that would favourably affect the pharmacological properties of said compounds of the present invention. Those compounds having favourable pharmacological properties would be apparent to the pharmaceutical chemist, i.e. those that are non-toxic and that possess such pharmacological properties to provide sufficient palatability, absorption, distribution, metabolism and excretion. Other factors, more practical in nature, that are important in the selection are cost of raw materials, ease of crystallisation, yield, stability, hygroscopicity, and flowability of the resulting bulk drug.

Representative acids that may be used in the preparation of pharmaceutically acceptable salts include but are not limited to the following: acetic acid, 2,2-dichlorolactic acid, acylated amino acids, adipic acid, alginic acid, ascorbic acid, L-aspartic acid, benzenesulphonic acid, benzoic acid, 4-acetamidobenzoic acid, (+)-camphoric acid, camphorsulphonic acid, (+)-(1S)-camphor-10-sulphonic acid, capric acid, caproic acid, caprylic acid, cinnamic acid, citric acid, cyclamic acid, dodecylsulphuric acid, ethane-1,2-disulphonic acid, ethanesulphonic acid, 2-hydroxy-ethanesulphonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hipuric acid, hydrobromic acid, hydrochloric acid, (+)-L-lactid acid, (±)-DL-lactic acid, lactobionic acid, maleic acid, (−)-L-malic acid, malonic acid, (±)-DL-mandelic acid, methanesulphonic acid, naphthalene-2-sulphonic acid naphthalene-1,5-disulphonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulphuric acid, tannic acid, (+)-L-tartaric acid, thiocyanic acid, p-toluenesulphonic acid and undecylenic acid.

Representative bases that may be used in the preparation of pharmaceutically acceptable salts include the following: ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Examples of suitable esters include $C_{1-7}$ alkyl, $C_{5-7}$ cycloalkyl, phenyl, substituted phenyl, and phenyl-$C_{1-6}$ alkyl esters. Preferred esters include methyl esters.

If $R^7$ is the group of formula (II), n is preferably 1. In a preferred embodiment, $R^8$ and $R^9$ are hydrogen atoms, while $R^{10}$ is a methyl group.

If $R^7$ is the group of formula (III), preferred combinations of q and r are for example q=1 and r=1, q=2 and r=0, and q=3 and r=0.

A preferred class of compounds is quinazoline compounds of the invention, wherein X and Y are $CR^3$, and Q and Z are N. Particularly preferred compounds are those quinazolines wherein at least three groups out of $R^3$, $R^4$, $R^5$ and $R^6$ are hydrogen atoms. Further preferred compounds are those quinazolines wherein $R^7$ is 4-methylpiperazino.

Another preferred class of compounds is quinoline compounds of the invention, wherein X is $CR^1$ and Y is $CR^3$. Particularly preferred compounds are those quinolines wherein $R^1$, $R^2$, $R^3$, $R^5$ and $R^6$ are hydrogen atoms. It is further preferred that $R^7$ is 4-methylpiperazino.

R' is preferably $NR^yR^z$ including heteroaryl (optionally substituted) or heterocyclic such as morpholino. Alternatively, one or both or $R^y$ and $R^z$ may be H. Examples of $SO_2R'$ are R' may include fused ring structures. An example is dihydroindolyl.

Table 1 illustrates compounds of the invention. In the column "Activity Class" the following signs have the following meaning: "-" refers to a $K_i$ (the constant of inhibition in an $H_4$ binding assay (see the working examples hereinabove)>10 μM; "+/−" means 10 μM<$K_i$<1 μM and "+" means $K_i$<1 μM.

TABLE 1

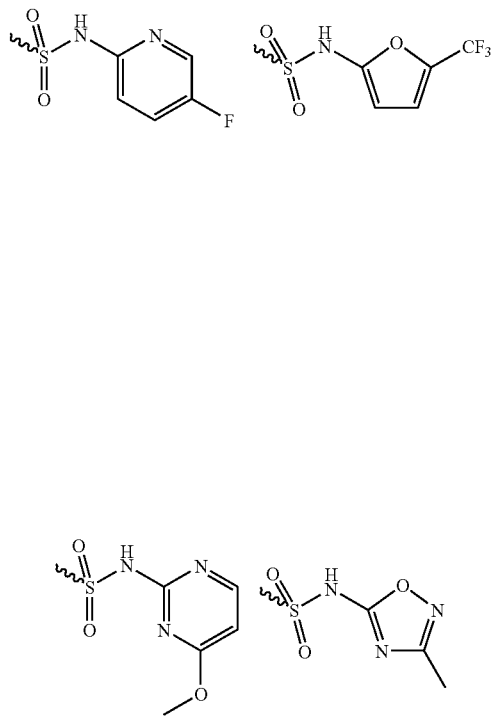

| Nr | Code | R1 | R2 | Activity Class* |
|---|---|---|---|---|
| 1 | 10512 | | 6-Cl | + |
| 2 | 10519 | | 6-Cl | + |
| 3 | 10514 | | 6-Cl | + |
| 4 | 10571 | | 6-Cl | + |
| 5 | 10570 | | 6-Cl | + |
| 6 | 10558 | | 6-Cl | + |
| 7 | 10657 | | 6-Cl | + |
| 8 | 10656 | | 6-Cl | + |
| 9 | 10646 | | 6-Cl | + |

TABLE 1-continued new quinazoline compounds

[Structure: quinazoline with R2 substituent, N-methylpiperazine at 2-position, R1 at 4-position]

| Nr | Code | R1 | R2 | Activity Class* |
|---|---|---|---|---|
| 10 | 10517 | NH-CH₂CH₂CH₂-S(=O)(=N-CH₃)-OH | 6-Cl | + |
| 11 | 10775 | NH-CH₂CH₂-S(=O)(=N-Ph)-OH | 5-CF₃ | + |
| 12 | 10660 | NH-CH₂CH₂-S(=O)(=N-Ph)-OH | 6,7-Cl | + |
| 13 | 10776 | NH-CH₂CH₂-S(=O)(=N-Ph)-OH | 6-Br, 7-Cl | + |
| 14 | 10658 | NH-CH₂CH₂-S(=O)(=N-Ph)-OH | 6,8-Cl | + |
| 15 | 10659 | NH-CH₂CH₂-S(=O)(=N-Ph)-OH | 6-I | + |
| 16 | 10781 | NH-CH₂CH₂-S(=O)(=N-Ph)-OH | 7,8-Cl | + |
| 17 | 10782 | NH-CH₂CH₂-S(=O)(=N-Ph)-OH | 5,7-Cl | + |

The present invention includes prodrugs of the compounds of the invention. In general, such prodrugs will be functional derivatives of the compounds that are readily convertible in vivo into the bio-active compound. Thus, in the uses of the compounds for methods of treatment of the present invention, the term "administering" shall encompass the treatment of the various disorders described with the compound specifically disclosed or with a compound that may not be specifically disclosed, but that converts to the specified compound in vivo after administration to the patient. Analogously, the term "compound", when applied to compounds of this invention, encompasses any specific compound according to the present invention or any compound (or prodrug) that converts to the specifically disclosed compound in vivo after administration, even if such prodrug is not explicitly disclosed herein.

Compounds of the present invention are antagonists, inverse agonists or agonists, including partial agonists, of histamine $H_4$ receptors. Thus, these compounds reversibly or irreversibly bind to the histamine $H_4$ receptor. Further, some compounds may possess affinity for the histamine $H_1$ receptor in addition to $H_4R$ affinity. Such compounds may be able to modulate inflammatory diseases with both a $H_4R$ and $H_1R$ component more efficiently than only selective $H_1R$ or selective $H_4R$ ligands. Without wishing to be bound by theory, this is considered to be indicative of therapeutic utility.

The effect of an antagonist may also be obtained by an inverse agonist or a partial agonist. Inverse agonism describes the property of a compound to actively turn off a receptor that displays constitutive activity. Constitutive activity can be identified in cells that have been forced to over-express the human $H_4$ receptor. Constitutive activity can be measured by measuring cAMP (cyclic adenosine monophosphate) levels or by measuring a reporter gene sensitive to cAMP levels after a treatment with a cAMP stimulating agent such as forskolin. Cells that over-express $H_4$ receptors will display lower cAMP levels after forskolin treatment than non-expressing cells. Compounds that behave as $H_4$ agonists will dose-dependently lower forskolin-stimulated cAMP levels in $H_4$-expressing cells. Compounds that behave as $H_4$ inverse agonists will dose-dependently stimulate cAMP levels in $H_4$-expressing cells. Compounds that behave as $H_4$ antagonists will block either $H_4$ agonist induced inhibition of cAMP or $H_4$ inverse agonist induced increases in cAMP.

Compounds of the invention may be administered to a subject, in therapy, e.g. for the treatment of inflammation.

"Inflammation" as used herein refers to the response that develops as a consequence of release of inflammatory mediators, such as histamine, serotonin, leukotrienes, prostaglandins, cytokines, chemokines, which in turn is caused by at least one stimulus, which can be for example an immunological stimulus or a non-immunological stimulus.

The term "subject" as used herein includes animals and in particular mammals including and preferably being a human, a dog, a cat, a horse, a rat, a rabbit, a mouse, and a non-human primate, which animal is in need of observation, experiment, treatment or prevention in connection with the relevant disease or condition.

The term "composition" as used in this application includes a product comprising the specified ingredients in the specified amounts, including in the therapeutically effective amounts, as well as any product that results directly or indirectly from combinations of the specified ingredients in the specified amounts.

The term "therapeutically effective amount" as used in this description and the appending claims is meant to be that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The compounds of the invention are useful for the amelioration of symptoms associated with the treatment and/or the prevention of conditions and diseases such as inflammatory disorders, allergic disorders, dermatological disorders, autoimmune disease, lymphatic disorders, immunodeficiency disorders and cancer, including the more specific conditions and diseases given above.

The invention is also directed to a pharmaceutical composition for treating or preventing an $H_4$ receptor-mediated condition in a subject, comprising a therapeutically effective amount for treating, reducing or preventing an $H_4$ receptor-mediated condition of at least one $H_4$ receptor antagonist or partial agonist or inverse agonist according to the present invention. Such pharmaceutical compositions typically also comprise a pharmaceutically acceptable carrier.

In addition, the invention features an anti-inflammatory composition, comprising a therapeutically effective amount for treating or preventing inflammation of at least one anti-inflammatory compound according to the present invention. These compositions typically also comprise a pharmaceutically acceptable carrier.

Another example of the invention is the use of a compound according to the present invention in the preparation of a medicament for treating any one of the conditions referred to herein; one of such conditions is inflammation. Another example of the invention is the use of a compound according to the present invention in the treatment or prevention of any one of the conditions referred to herein; one of such conditions is inflammation.

The invention is also directed to a method for treating or preventing inflammation in a subject, comprising administering to a subject in connection with an inflammatory response a pharmaceutical composition that comprises a therapeutically effective amount of at least one anti-inflammatory compound according to the present invention.

The invention also features methods for treating or preventing an $H_4$ receptor-mediated condition in a subject, comprising administering to the subject a pharmaceutical composition that comprises a therapeutically effective amount of at least one $H_4$ receptor antagonist, partial agonist or inverse agonist according to the present invention.

Embodiments of methods for treating or preventing inflammation in a subject that comprise administering to the subject in connection with an inflammatory response a pharmaceutical composition comprising a therapeutically effective amount of at least one anti-inflammatory compound according to the present invention include methods wherein at least one of the following is satisfied: said inflammatory response is a response to a physical stimulus; said inflammatory response is a response to a chemical stimulus; said inflammatory response is a response to infection; said inflammatory response is a response to an invasion by a body that is foreign to said subject; said inflammatory response is a response to an immunological stimulus; said inflammatory response is a response to a non-immunological stimulus; said inflammatory response is a response to at least one of the conditions: allergy, asthma, chronic obstructed pulmonary disease, atherosclerosis, rheumatoid arthritis, multiple sclerosis, inflammatory bowel disease, and more specifically wherein said inflammatory bowel disease is at least one of Crohn's disease and ulcerative colitis, psoriasis, allergic rhinitis, scleroderma, autoimmune thyroid disease, immune-mediated diabetes mellitus, and lupus; said inflammatory response is a response to at least one of the conditions: myasthenia gravis, autoimmune neuropathy, and more specifically wherein said autoimmune neuropathy is Guillain-Barré neuropathy, autoimmune uveitis, autoimmune haemolytic anemia, pernicious anemia, autoimmune thrombocytopenia, temporal arteritis, anti-phospholipid syndrome, vasculitides, and more specifically wherein said vasculitides is Wegener's granulomatosis, Bechet's disease, dermatitis herpetiformis, pemphigus vulgaris, vitiligio, primary biliary cirrhosis, autoimmune hepatitis, autoimmune oophoritis, autoimmune orchitis, autoimmune disease of the adrenal gland, polymyositis, dermatomyositis, spondyloarthropathy, and more specifically wherein said spondyloarthropathy is ankylosing spondylitis, and Sjogren's syndrome; said inflammatory response is acute inflammation; said inflammatory response is chronic inflammation. Moreover, the compounds of the invention can be used in the treatment of or therapy against cancer. In yet a further embodiment, the compounds of the invention can be used to reduce, suppress or avoid itch. Pruritis is a disease that is caused by both a $H_1R$ and $H_4R$ component and may benefit from such dual action ligands. Administration "in connection with" an inflammatory response according to the present invention includes administration at a time that it is at least one of prior to, at the onset of, and after inflammation is detected.

Aspects of the invention include (a) a pharmaceutical composition comprising at least one compound according to the invention and a pharmaceutically acceptable carrier; (b) a packaged drug comprising (1) a pharmaceutical composition comprising at least a compound according to the present invention and a pharmaceutically acceptable carrier, and (2) instructions for the administration of said composition for the treatment or prevention of any one of the conditions referred to herein, such as an $H_4$-mediated disease or condition, and more particularly inflammation.

This invention provides methods for treating, reducing or preventing an $H_4$-mediated condition in a subject, said methods comprising administering to the subject a pharmaceutically effective amount of a composition comprising at least one compound according to the invention. In these conditions, the action of the $H_4$ receptor is involved. For example, the invention features a method for treating an $H_4$ mediated condition in a subject, said method comprising administering to the subject a pharmaceutically effective $H_4$-antagonising amount of a composition comprising at least one compound according to the invention. As used herein "treating" a disorder means eliminating, reducing or otherwise ameliorating the cause and/or effects thereof. Terms such as to "inhibit" the onset of a disorder or event, and to "prevent" a disorder or condition mean preventing, delaying or reducing the likelihood of such onset.

The term "unit dose" is used herein to refer to physically discrete units suitable as unitary dosages for subjects, each unit containing a predetermined effective, pharmacologic effective amount of the active ingredient calculated to produce the desired pharmacological effect. The specifications for the novel unit dosage forms of this invention are determined by, and are directly dependent on, the characteristics of the active ingredient, and on the limitations inherent in the art of compounding such an active ingredient for therapeutic use in subjects.

The pharmaceutical compositions can be prepared using conventional pharmaceutical excipients and compounding techniques. Examples of suitable unit dosage forms are tables, capsules, pills, powders, powder packets, granules, wafers, and the like, segregated multiples of any unit dosage form, as well as liquid solutions, and suspensions. Some liquid forms are aqueous, whereas other embodiments of liquid forms are non-aqueous. Oral dosage forms may be elixirs, syrups, capsules, tablets and the like. Examples of solid carriers include those materials usually employed in the manufacture of pills or tablets, such as lactose, starch, glucose, methylcellulose, magnesium stearate, dicalcium phosphate, mannitol and the like, thickeners such as tragacanth and methylcellulose USP, finely divided $SiO_2$, polyvinylpyrrolidone, magnesium stearate, and the like. Typical liquid oral excipients include ethanol, glycerol, water and the like. All excipients may be mixed as needed with diluents (for example, sodium and calcium carbonates, sodium and calcium phosphates, and lactose), disintegrants (for example, cornstarch and alginic acid), granulating agents, lubricants (for example magnesium stearate, stearic acid, and talc), binders (for example starch and gelatine), thickeners (for example paraffin, waxes, and petrolatum), flavouring agents, colouring agents, preservatives, and the like by conventional techniques known to those of ordinary skill in the art of preparing dosage forms. Coatings can be present and include for example glyceryl monostearate and/or glyceryl distearate. Capsules for oral use include hard gelatine capsules in which the active ingredient is mixed with a solid diluent, and soft gelatine capsules, in which the active ingredient is mixed, with water or an oil, such as peanut oil, liquid paraffin, or olive oil.

Parenteral dosage forms may be prepared using water or another sterile carrier. Parenteral solutions can be packaged in containers adapted for subdivision into individual doses. For intramuscular, intraperitoneal, subcutaneous, and intravenous use, the compounds according to the invention will be generally provided in sterile aqueous solutions or suspensions, buffered to an appropriate pH and isotonicity. Suitable aqueous vehicles include Ringer's solution and isotonic sodium chloride. Aqueous suspensions may include suspending agents such as cellulose derivatives, sodium alginate, polyvinyl-pyrrolidone, and gum tragacanth, and a wetting agent, such as lecithin. Suitable preservatives for aqueous suspensions include ethyl and n-propyl p-hydroxybenzoate. Parenteral formulations include pharmaceutically acceptable aqueous or non-aqueous solutions, dispersions, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbants, (h) lubricants, (i) buffering agents, and (j) propellants.

Compositions may also contain adjuvants such as preserving, wetting, emulsifying, and dispensing agents; antimicrobial agents such as parabens, chlorobutanol, phenol, and sorbic acid; isotonic agents such as sugar or sodium chloride; absorption-prolonging agents such as aluminium monostearate and gelatine; and absorption-enhancing agents.

Physiologically acceptable carriers are well known in the art. Examples of liquid carriers are solutions in which compounds according to the invention form solutions, emulsions, and dispersions. Compatible antioxidants, such as methylparaben and propylparaben, can be present in solid and/or liquid compositions, as can sweeteners.

Pharmaceutical compositions according to the invention may include suitable emulsifiers typically used in emulsion compositions. Gelling agents may also be added to compositions according to this invention. Polyacrylic acid derivatives, such as carbomers, are examples of gelling agents, and more particularly, various types of carbopol. Suspensions may be prepared as a cream, an ointment, including a water-free ointment, a water-in-oil emulsion, an oil-in-water emulsion, and emulsion gel, or a gel.

Compounds according to the present invention can be administered by oral or parenteral routes, including intravenous, intramuscular, intraperitoneal, subcutaneous, rectal, intracisternal, intravaginal, intravesical, topical or local administration, and by inhalation (bucal or nasal, preferably in the form of a spray). For oral administration, the compounds according to the invention will be generally provided in the form of tablets, capsules, or as a solution or suspension. Other methods of administration include controlled release formulations, such as subcutaneous implants and dermal patches.

Pharmaceutically effective doses of the compounds according to the invention may be ascertained by conventional methods. The specific dosage level required for any particular subject will depend on a number of factors, including severity of the condition, type of symptoms needing treatment, the route of administration, the weight, age, and general condition of the subject, and the administration of other medicaments.

In general, the daily dose (whether administered as a single dose or as divided doses) will be in the range of from about 0.01 mg to about 1000 mg per day, more usually from about 1 mg to about 500 mg per day, and most usually from about 10 mg to about 200 mg per day. Expressed as dosage per unit body weight, a typical dose will be expected to be between about 0.0001 mg/kg and about 15 mg/kg, especially between about 0.01 mg/kg and about 7 mg/kg, and most especially between about 0.15 mg/kg and 2.5 mg/kg.

Oral dose ranges include from about 0.01 to 500 mg/kg, daily, more preferably from about 0.05 to about 100 mg/kg, taken in 1-4 separate doses. Some compounds of the invention may be orally dosed in the range of about 0.05 to about 50 mg/kg daily, while others may be dosed at 0.05 to about 20 mg/kg daily. Infusion doses can range from about 1.0 to about $1.0 \times 10^4$ μg/(kg·min) of inhibitor, admixed with a pharmaceutical carrier over a period ranging from several minutes to several days. For topical administration, compounds of the present invention may be mixed with a pharmaceutical carrier at a concentration from about 0.1 to about 10% of drug to vehicle. Capsules, tablets or other formulations (such as liquids and film-coated tablets) may be of between 0.5 and 200 mg, such as 1, 3, 5, 10, 15, 25, 35, 50 mg, 60 mg, and 100 mg and can be administered according to the disclosed methods. Daily dosages are envisaged to be, for example between 10 mg and 5000 mg for an adult human subject of normal weight.

The compounds of the invention can be prepared according to processes within the skill of the art and/or according to processes of this invention, such as those described in the schemes and examples that follow and by matrix or combinatorial methods.

Illustrative preparations are presented in the following Schemes. Other compounds of the invention may be made in the same general way, using modifications that will be apparent to those of ordinary skill in the art.

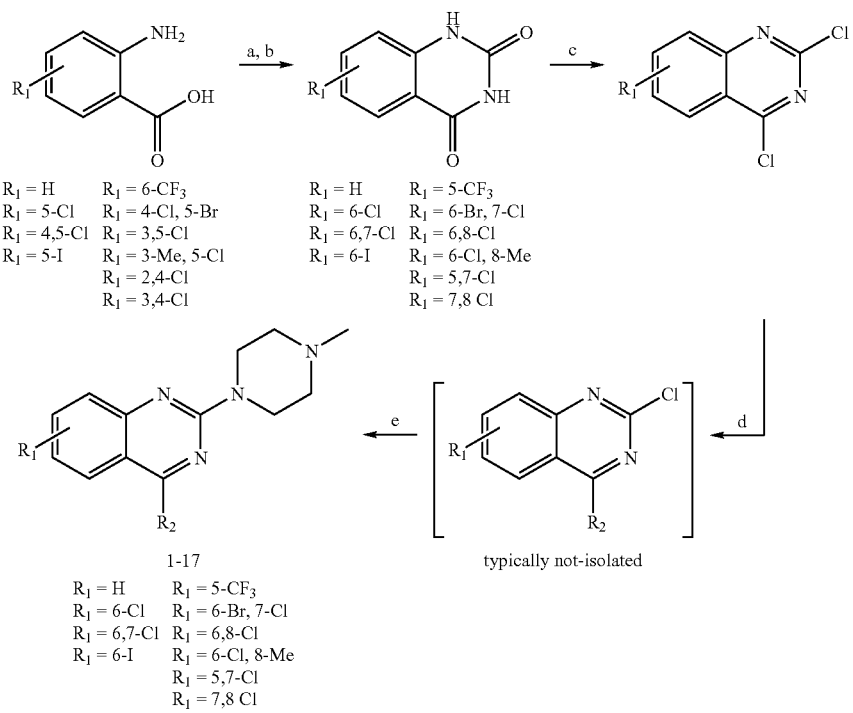

Scheme 1[a]

[a] Reagents and conditions: a) urea, 160° C.; b) 0.5M NaOH; c) DIPEA, POCl₃, reflux; d) various amines, DIPEA, EtOAc r.t.; e) N-methylpiperazine, microwave, 120-° C.

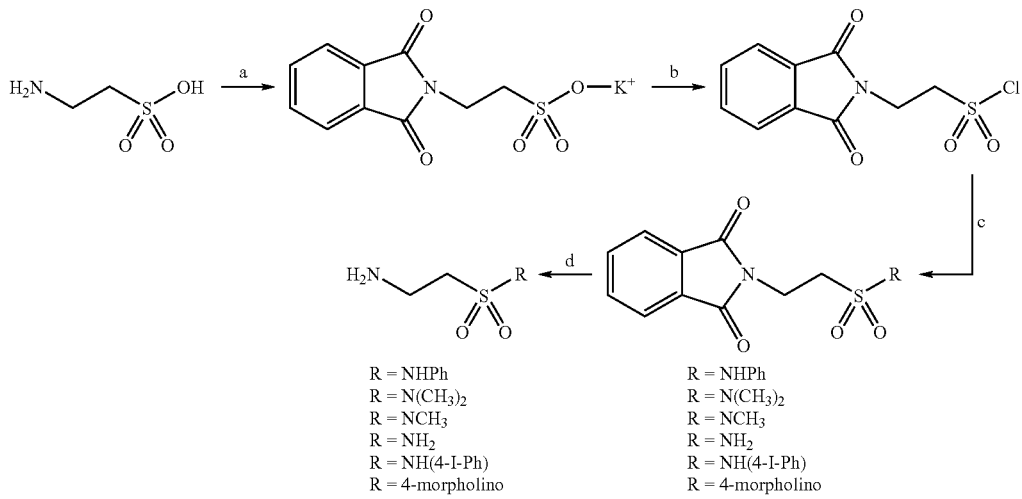

Scheme 2[a]

[a] Reagents and conditions: a) phthalic anhydride, KOAc, AcOH; b) PCl₃, toluene, reflux; c) various amines, CHCl₃, r.t; d) H₂NNH₂, EtOH, reflux.

The following Examples illustrate the invention.

3-phthalimidopropanesulfonyl chloride

Potassium-3-phthalimidopropane-1-sulfonate (6.0 g) was suspended in dry toluene (25 ml) under a nitrogen atmosphere and heated to reflux. Then 4.11 g of $PCl_5$ was added in portions and the mixture was heated at reflux for 60 minutes. A second portion of 4.11 g of $PCl_5$ was added and heating was continued for 90 minutes. The reaction mixture was evaporated to dryness and crushed ice was added to the residual solid. When the ice had just molten, the solid was filtered off and dried in vacuo to yield 5.64 g (87%) of a solid. $^1$H-NMR $(CDCl_3)$ δ (ppm) 7.88-7.81 (m, 2H), 7.78-7.71 (m, 2H), 3.87 (t, J=6.5 Hz, 2H), 3.77-3.69 (m, 2H), 2.48-2.34 (m, 2H).

potassium 3-phthalimidopropane-1-sulfonate

Starting from 3-amino-1-propanesulfonic acid (3.0 g) this compound was prepared according to a procedure described for 3-phthalimidoethanesulfonyl chloride in literature: Winterbottom et al. Studies in chemotherapy. XV. Amides of pantoyl turine. *JACS*, (1947), 1393-1401. Yield: 6.09 g (98%). $^1$H-NMR (D$_2$O) δ (ppm) 7.74 (s, 4H), 3.71 (t, J=6.9 Hz, 2H), 2.97-2.89 (m, 2H), 2.12-1.98 (m, 2H).

General Method A

Synthesis of Phthalimido Sulfonamides from their Corresponding Sulfonyl Chloride Precursors. The Following Procedure Described for 2-phthalimidoethane-n-phenylsulfonamide is Representative for the Synthesis of Intermediate Sulfonamides

2-phthalimidoethane-N-phenylsulfonamide

2-Phthalimidoethanesulfonyl chloride (2.0 g) was added in portions to a solution of aniline (2.3 g) in chloroform (15 ml) and the resulting mixture was stirred at room temperature for 16 hours. The organic phase was then washed with water and 1 M HCl. Removal of the solvent gave the crude product as a solid that was recrystallised from EtOH to yield 1.76 g (65%) of the title compound as a solid. $^1$H-NMR (CDCl$_3$) δ (ppm) 7.87-7.83 (m, 2H), 7.77-7.70 (m, 2H), 7.32-7.10 (m, 5H), 4.09-4.03 (m, 2H), 3.47-3.41 (m, 2H).

2-phthalimidoethanesulfonamide

2-Phthalimidoethanesulfonyl chloride (2.0 g) was added portion wise to a solution of 0.5 M of ammonia in dioxane (15 ml) and the solution obtained this way was stirred at room temperature. After 48 hours the reaction mixture was poured in water (50 ml) causing the title compound to precipitate. The product was collected by filtration. Yield: 1.52 g (83%) of a solid. $^1$H-NMR (DMSO-δ$_6$) δ (ppm) 7.92-713 (m, 4H), 7.06 (s, 2H), 6.88-3.93 (m, 2H), 3.37-3.30 (m, 2H).

2-(2-(morpholinosulfonyl)ethyl)isoindole-1,3-dione

Prepared according to general method A from 2-phthalimidoethanesulfonyl chloride (2.0 g) and morpholine (2.14 ml). Yield: 1.28 g (48%). $^1$H-NMR (CDCl$_3$) δ (ppm) 7.94-7.84 (m, 4H), 3.99 (t, J=6.8 Hz, 2H), 3.62 (t, J=4.7 Hz, 4H), 3.45 (t, J=6.8 Hz, 4H), 3.15 (t, J=4.6 Hz, 4H).

2-phthalimidoethane-N-(4-iodophenyl)sulfonamide

Prepared according to general method A from 2-phthalimidoethanesulfonyl chloride (1.50 g) and 4-iodoaniline (2.70 g). Yield: 1.56 g (56%). $^1$H-NMR (CDCl$_3$) δ (ppm) 10.14 (s, 1H), 7.83 (s, 4H), 7.63 (d, J=8.7 Hz, 2H), 7.00 (d, J=8.8 Hz, 2H), 3.94 (t, J=7.1 Hz, 2H), 3.94-3.44 (m, 2H).

3-phthalimidopropane-N-methylsulfonamide

Synthesised according to the method described for 2-phthalimidoethane-N-methylsulfonamide from 3-phthalimidopropanesulfonyl chloride (2.50 g). Yield: 854 mg (35%). $^1$H-NMR (CDCl$_3$) δ (ppm) 7.82-7.76 (m, 2H), 7.72-7.64 (m, 2H), 4.13 (br s, 1H), 3.78 (t, J=6.8 Hz, 2H), 3.07-2.99 (m, 2H), 2.74 (d, J=5.2 Hz, 3H), 2.21-1.18 (m, 2H).

2-phthalimidoethane-N-methylsulfonamide

2-Phthalimidoethanesulfonyl chloride (2.0 g) was added portion wise to a solution of 2.0 M methylamine in THF (15 ml) and the solution obtained this way was stirred at room temperature. After 48 hours the reaction mixture was poured in water (50 ml) causing the title compound to precipitate. The product was collected by filtration and recrystallized from EtOH:water, 50:1 to yield: 1.04 g (48%) of the desired product as a solid.

2-phthalimidoethane-N,N-dimethylsulfonamide

2-Phthalimidoethanesulfonyl chloride (2.0 g) was used in a procedure similar to the one used for 2-phthalimidoethane-N-methylsulfonamide. Yield: 1.03 g (45%). $^1$H-NMR (CDCl$_3$) δ (ppm) 7.87-7.79 (m, 2H), 7.75-7.66 (m, 2H), 4.11 (t, J=, 2H), 3.30 (t, J=Hz, 2H), 2.87 (s, 6H).

General Method B

Deprotection of Phthalimido Sulfonamides to their Corresponding Primary Amines. The Following Procedure is Representative for the Synthesis of Aminoethane- or Aminopropane Sulfonamides

2-aminoethanesulfonamide hydrochloride

A suspension of 2-phthalimidoethanesulfonamide (1.52 g) was heated at reflux in EtOH (30 ml) after which hydrazine (0.36 ml) (64% in water) was added. After 3 hours a precipitate formed that was removed by filtration. The filtrate was evaporated to dryness and added to water (150 ml). The aqueous suspension was acidified with conc. HCl and residual insoluble material was filtered off. The filtrate was evaporated to dryness and the crude sulfonamide was recrystallized from EtOH/water (9:1) to yield the final product as 764 mg (64%) of a solid. $^1$H-NMR (D$_2$O) δ (ppm) 3.62-3.55 (m, 2H), 3.51-3.44 (m, 2H).

3-aminopropane-N-methylsulfonamide hydrochloride

Prepared according to general method B from 3-phthalimidopropane-N-methylsulfonamide (847 mg). Yield: 500 mg (88%). $^1$H-NMR (D$_2$O) δ (ppm) 3.31 (t, J=7.5 Hz, 2H), 3.15 (t, J=7.7 Hz, 2H), 2.72 (s, 3H), 2.13 (p, J=7.5 Hz, 2H).

2-aminoethane-N-methylsulfonamide hydrochloride

Prepared according to general method B from 3-phthalimidoethane-N-methylsulfonamide (1.03 g). Yield: 415 mg (72%). $^1$H-NMR (D$_2$O) δ (ppm) 3.53-3.46 (m, 2H), 3.43-3.40 (m, 2H), 2.73 (s, 3H).

2-aminoethane-N,N-dimethylsulfonamide hydrochloride

Prepared according to general method B from 3-phthalimidopropane-N,N-dimethylsulfonamide (1.03 g). Yield: 602 mg (87%). $^1$H-NMR (D$_2$O) δ (ppm) 3.49 (s, 4H), 2.89 (s, 6H); $^{13}$C NMR (D$_2$O) δ (ppm) 45.61, 38.31, 35.36.

2-aminoethane-N-phenylsulfonamide

Prepared according to general method B from 2-phthalimidoethane-N-phenylsulfonamide (1.60 g). The filtrate that was evaporated to dryness was not added to water but was sufficiently pure to be used in the next step without further purification. Yield: 386 mg (40%) of a solid. $^1$H-NMR (DMSO-$d_6$) δ (ppm) 7.36-7.04 (m, 5H), 3.14 (t, J=7.0 Hz, 2H), 2.88 (t, J=6.7 Hz, 2H).

2-(morpholinosulfonyl)ethanamine hydrochloride

Prepared according to general method B from 2-(2-(morpholinosulfonyl)ethyl)isoindole-1,3-dione (1.23 g). Yield: 429 mg (57%).

2-aminoethane-N-(4-iodophenyl)sulfonamide hydrochloride

Prepared according to general method B from 2-phthalimidoethane-N-(4-iodophenyl)sulfonamide (1.47 g). The title compound was obtained after recrystallisation of the crude hydrochloride salt from water. Yield: 704 mg (60%). $^1$H-NMR (DMSO-$d_6$) δ (ppm) 8.17 (br m, 3H), 7.70 (d, J=8.5 Hz, 2H), 7.07 (d, J=8.6 Hz, 2H), 3.49-3.42 (m, 2H), 3.10 (m, 2H).

General Method C

Synthesis of Quinazoline-Diones from their Corresponding Anthranilic Acid Precursors. The Following Procedure Described for 6,7-dichloroquinazolin-2,4(1H,3H)-dione is Representative for the Synthesis of Intermediate Quinazolinediones 6,7-dichloroquinazolin-2,4(1H,3H)-dione 2-Amino-4,5-dichlorobenzoic acid (920 mg) and urea (2.75 g) were stirred at 160° C. After 6 hours the mixture was cooled to 100° C. and an equivalent volume of water was added while stirring was continued for 5 minutes. The formed precipitate was filtered off and washed with water to yield a solid cake that was suspended in a solution of 0.5 N NaOH in water. The suspension was heated to boil for 5 minutes and then cooled to r.t. The pH was adjusted to about 2 with HCl and the quinazoline-dione was filtered off. After washing with a mixture of water and methanol the product was dried in vacuo to yield 994 mg (94%) of a solid. $^1$H-NMR (DMSO-$d_6$) δ (ppm) 7.89 (s, 1H), 7.33 (s, 1H).

6,8-dichloroquinazolin-2,4(1H,3H)-dione

Prepared according to general method C from 2-amino-3,5-dichlorobenzoic acid (3.0 g) and urea (8.8 g). Yield: 3.20 g (95%) of a solid. Although it contained a small amount of an impurity it was used in the next step without further purification. $^1$H-NMR (DMSO-$d_6$) δ (ppm) 10.13 (br s, 1H), 7.58 (d, J=2.5 Hz, 1H), 7.50 (d, J=2.6 Hz, 1H).

7,8-dichloroquinazolin-2,4(1H,3H)-dione

Prepared according to general method C from 2-amino-3,4-dichlorobenzoic acid (2.23 g) and urea (6.49 g). Yield 2.18 g (87%) of a solid. $^1$H-NMR (DMSO-$d_6$) δ (ppm) 11.64 (br s, 1H), 10.87 (br s, 1H), 7.86 (d, J=8.5 Hz, 1H), 7.43 (d, J=8.5 Hz, 1H).

5,7-dichloroquinazolin-2,4(1H,3H)-dione

Prepared according to general method C from 6-amino-2,4-dichlorobenzoic acid (2.0 g) and urea (5.83 g). Yield 1.72 g (77%) of a solid. $^1$H-NMR (DMSO-$d_6$) δ (ppm) 11.39 (br s, 2H), 7.32 (d, J=2.0 Hz, 1H), 7.15 (d, J=2.0 Hz, 1H).

6-iodoquinazolin-2,4(1H,3H)-dione

Prepared according to general method B from 2-amino-5-iodobenzoic acid (5.0 g) and urea (11.4 g). Yield: 5.34 g (98%) of a solid. $^1$H-NMR (DMSO-$d_6$) δ (ppm) 8.04 (d, J=2.0 Hz, 1H), 7.77 (dd, J=2.1 Hz, J=8.6 Hz, 1H), 6.90 (d, J=8.6 Hz, 1H).

5-trifluoromethylquinazolin-2,4(1H,3H)-dione

Prepared according to general method C from 2-amino-6-trifluoromethylbenzoic acid (1.0 g) and urea (2.92 g). Yield: 948 mg (85%) of a solid. $^1$H-NMR (DMSO-$d_6$) δ (ppm) 11.43 (br s, 2H), 7.78 (t, J=7.9 Hz, 1H), 7.58 (d, J=7.4 Hz, 1H), 7.48 (d, J=8.2 Hz, 1H).

6-bromo-7-chloroquinazolin-2,4(1H,3H)-dione

Prepared according to general method C from 2-amino-5-bromo-4-chlorobenzoic acid (987 mg) and urea (2.36 g). Yield: 1.00 g (92%) of a solid. $^1$H-NMR (DMSO-$d_6$) δ (ppm) 8.01 (s, 1H), 7.36 (s, 1H).

General Method D

Synthesis of 2,4-dichloroquinazolines From Their Corresponding Quinazoline-Dione Precursors. The Following Procedure Described for 2,4,6,7-tetrachloroquinazoline Representative for the Synthesis of 2,4-dichloroquinazoline Intermediates 2,4,6,7-tetrachloroquinazoline 6,7-Dichloroquinazolin-2,4(1H,3H)-dione (800 mg), DIPEA (1.23 ml) and POCl$_3$ (4.0 ml) were heated at reflux. After 3 hours the reaction mixture was cautiously poured over crushed ice and stirred vigorously. This aqueous mixture was extracted with CH$_2$Cl$_2$ DCM and the combined organic layers were washed with brine and dried over Na$_2$SO$_4$. Evaporation of the solvent gave a solid that was redissolved in CH$_2$Cl$_2$ after which it was filtered over a pad of silica using CH$_2$Cl$_2$ as eluent. Removal of the organic phase gave the product as 657 mg (71%) of a solid. $^1$H-NMR (CDCl$_3$) δ (ppm) 8.34 (s, 1H), 8.31 (s, 1H); $^{13}$C-NMR (CDCl$_3$) δ (ppm) 162.67, 156.22, 150.56, 141.75, 134.24, 128.98, 126.55, 121.28.

2,4,6,8-tetrachloroquinazoline

Prepared according to general method D from 6,8-dichloroquinazolin-2,4(1H,3H)-dione (1.544 g). Yield: 992 mg (55%). $^1$H-NMR (CDCl$_3$) δ (ppm) 8.15 (d, J=2.2 Hz, 1H), 8.02 (d, J=2.2 Hz, 1H); $^{13}$C-NMR (CDCl$_3$) δ (ppm) 160.31, 144.80, 143.20, 134.25, 131.16, 130.88, 124.24, 123.34.

2,4,7,8-tetrachloroquinazoline

Prepared according to general method D from 7,8-dichloroquinazolin-2,4(1H,3H)-dione (1.0 g). Yield: 1.03 g (87%). $^1$H-NMR (CDCl$_3$) δ (ppm) 8.11 (d, J=9.0 Hz, 1H), 7.75 (d, J=9.0 Hz, 1H); $^{13}$C-NMR (CDCl$_3$) δ (ppm) 164.16, 156.83, 149.78, 141.15, 130.94, 130.44, 124.53, 121.61.

2,4,5,7-tetrachloroquinazoline

Prepared according to general method D from 5,7-dichloroquinazolin-2,4(1H,3H)-dione (1.0 g). Yield: 1.00 g (87%).

¹H-NMR (CDCl₃) δ (ppm) 87.86 (d, J=2.1 Hz, 1H), 7.70 (d, J=2.1 Hz, 1H); ¹³C-NMR (CDCl₃) δ (ppm) 162.09, 156.06, 154.54, 141.29, 132.48, 132.44, 126.78, 118.71.

2,4-dichloro-6-iodoquinazoline

Prepared according to general method D from 6-iodoquinazolin-2,4(1H,3H)-dione (2.0 g). Yield: 1.73 g (87%); ¹H-NMR (CDCl₃) δ (ppm) 8.59 (d, J=1.9 Hz, 1H), 8.19 (dd, J=1.9 Hz, J=8.9 Hz, 1H), 7.69 (d, J=8.9 Hz, 1H); ¹³C-NMR (CDCl₃) δ (ppm) 162.25, 155.27, 151.16, 144.80, 134.53, 129.18, 123.46, 94.52.

2,4-dichloro-5-trifluoromethylquinazoline

Prepared according to general method D from 5-trifluoromethylquinazolin-2,4(1H,3H)-dione (814 mg). Yield: 756 mg (80%). ¹H-NMR (CDCl₃) δ (ppm) 8.23-8.17 (m, 2H), 8.00 (t, J=7.9 Hz, 1H).

2,4,7-trichloro-6-bromoquinazoline

Prepared according to general method D from 6-bromo-7-chloroquinazolin-2,4(1H,3H)-dione (950 mg). Yield: 431 mg (40%). ¹H-NMR (CDCl₃) δ (ppm) 8.52 (s, 1H), 8.10 (s, 1H); ¹³C-NMR (CDCl₃) δ (ppm) 162.50, 156.26, 151.00, 143.34, 130.23, 128.57, 124.18, 121.45.

2,4,6-trichloro-quinazoline

Prepared according to general method D from 6-chloroquinazolin-2,4(1H,3H)-dione (1.41 g, 7.17 mmol) and N,N-diethylaniline (2.3 ml). Yield: 1.52 g (6.51 mmol, 91%). ¹H NMR (CDCl₃) (ppm) δ 8.23-8.22 (m, 1H), 7.97-7.87 (m, 2H); ¹³C-NMR (CDCl₃) δ (ppm) 162.50, 156.26, 151.00, 143.34, 130.23, 128.57, 124.18, 121.45.

General Method E

Synthesis of 2,4-Disubstituted Quinazolines from their Corresponding 2,4-dichloroquinazoline Precursors The following procedure described for 2-(6,7-dichloro-2-(4-methylpiperazin-1-yl)quinazoline-4-amino)-N-phenylethanesulfonamide (14) is representative for the synthesis of compounds 1-17.

When hydrochloric acid salts or other salts of the corresponding sulfonamide precursors are used, 3.1 equivalent of DIPEA are used instead of 2.1 for the example below.

Example 1

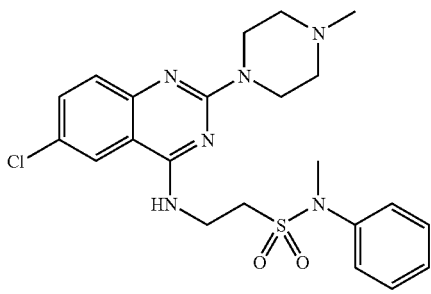 [SMILES: CN1CCN(c2nc(NCCS(=O)(=O)N(C)c3ccccc3)c3cc(Cl)ccc3n2)CC1]

2-(6-chloro-2-(4-methylpiperazin-1-yl)quinazoline-4-amino)-N-methyl-N-phenylethanesulfonamide Prepared according to general method E from 2,4,6-trichloroquinazoline (200 mg) and 2-aminoethane-N-methyl-N-phenylsulfonamide. Yield: 231 mg (57%). ¹H-NMR (CDCl₃) δ (ppm) 7.43-7.23 (m, 8H), 6.12 (m, 1H), 4.03 (q, J=6.0 Hz, 2H), 3.85 (t, J=5.0 Hz, 4H), 3.39-3.22 (m, 7H), 2.45 (t, J=5.0 Hz, 4H), 2.32 (s, 3H); ¹³C NMR (CDCl₃) δ 158.45, 150.72, 140.67, 133.16, 129.29, 127.47, 127.29, 126.16, 125.81, 120.18, 110.68, 54.96, 47.74, 46.13, 43.63, 38.24, 35.39; MS (ESI) m/z 475 (M+H)⁺.

Example 2

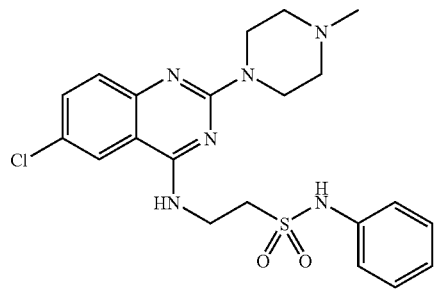 [SMILES: CN1CCN(c2nc(NCCS(=O)(=O)Nc3ccccc3)c3cc(Cl)ccc3n2)CC1]

2-(6-chloro-2-(4-methylpiperazin-1-yl)quinazoline-4-amino)-N-phenylethanesulfonamide Prepared according to general method E from 2,4,6-trichloroquinazoline (200 mg) and 2-aminoethane-N-phenylsulfonamide (172 mg). Yield: 312 mg (79%). ¹H-NMR (CDCl₃) δ (ppm) 7.41-7.07 (m, 8H), 6.20 (m, 1H), 4.00 (m, 2H), 3.80 (m, 4H), 3.52 (t, J=5.7 Hz, 2H), 2.41 (t, J=5.0 Hz, 4H), 2.30 (s, 3H); ¹³C-NMR (CDCl₃) δ (ppm) 158.57, 158.29, 150.63, 136.07, 133.20, 129.59, 127.26, 125.83, 125.32, 120.25, 110.62, 54.87, 49.89, 46.04, 43.56, 35.89; MS (ESI) m/z 385 (M+H)⁺.

Example 3

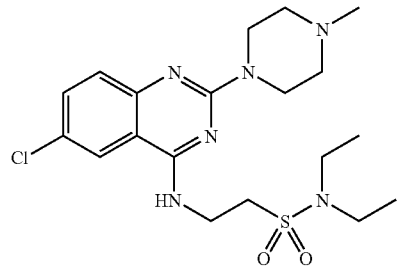 [SMILES: CCN(CC)S(=O)(=O)CCNc1nc(N2CCN(C)CC2)nc2ccc(Cl)cc12]

2-(6-chloro-2-(4-methylpiperazin-1-yl)quinazoline-4-amino)-N,N-diethylethanesulfonamide Prepared according to general method E from 2,4,6-trichloroquinazoline (200 mg) and 2-aminoethane-N,N-diethylsulfonamide oxalate (140 mg). Yield: 154 mg (74%). ¹H-NMR (CDCl₃) δ (ppm) 7.41-727 (m, 3H), 6.32 (m, 1H), 4.01 (q, J=5.8 Hz, 2H), 3.85 (t, J=4.9 Hz, 4H), 3.31-3.17 (m, 6H), 2.41 (t, J=4.9 Hz, 4H), 2.28 (s, 3H), 1.15 (t, J=7.1 Hz, 6H); $^{13}$C NMR (CDCl$_3$) δ 158.53, 150.69, 133.10, 127.24, 125.81, 120.23, 110.79, 54.97, 50.61, 46.11, 43.63, 41.41, 35.53, 14.24; MS (ESI) m/z 441 (M+H)$^+$.

Example 4

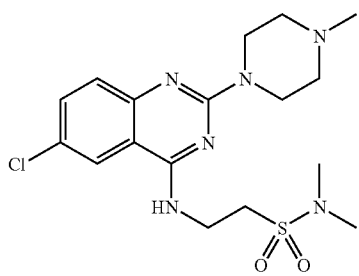 [SMILES: CN1CCN(c2nc(NCCS(=O)(=O)N(C)C)c3cc(Cl)ccc3n2)CC1]

2-(6-chloro-2-(4-methylpiperazin-1-yl)quinazoline-4-amino)-N,N-dimethylethanesulfonamide Prepared according to general method E from 2,4,6-trichloroquinazoline (200 mg) and 2-aminoethane-N,N-dimethylsulfonamide hydrochloride (162 mg). Yield: 117 mg (33%). $^1$H-NMR (CDCl$_3$) δ (ppm) 7.45-7.32 (m, 3H), 6.34 (m, 1H), 4.09 (q, J=5.8 Hz, 2H), 3.89 (t, J=5.0 Hz, 4H), 3.25 (t, J=6.0 Hz, 2H), 2.89 (s, 6H), 2.46 (t, J=5.0 Hz, 4H), 2.32 (s, 3H); $^{13}$C-NMR (CDCl$_3$) δ (ppm) 158.52, 150.73, 133.19, 127.33, 125.91, 120.15, 110.74, 54.96, 46.43, 46.10, 43.63, 37.28, 35.24; MS (ESI) m/z 413 (M+H)$^+$.

Example 5

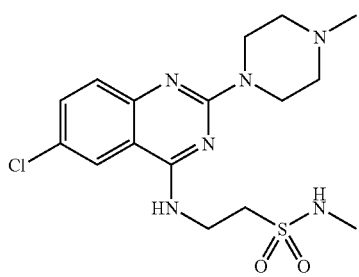 [SMILES: CNS(=O)(=O)CCNc1nc(N2CCN(C)CC2)nc2ccc(Cl)cc12]

2-(6-chloro-2-(4-methylpiperazin-1-yl)quinazoline-4-amino)-N-methylethanesulfonamide Prepared according to general method E from 2,4,6-trichloroquinazoline (200 mg) and 2-aminoethane-N-methylsulfonamide hydrochloride (131 mg). Yield: 117 mg (34%). $^1$H-NMR (MeOD) δ (ppm) 7.85 (d, J=2.3 Hz, 1H), 7.49 (dd, J=2.3 Hz, J=9.0 Hz, 1H), 7.35 (d, J=9.0 Hz, 1H), 3.99-3.89 (m, 6H), 3.46-3.31 (m, 2H), 2.71 (s, 3H), 2.52 (t, J=5.0 Hz, 4H), 2.34 (s, 3H); $^{13}$C-NMR (MeOD) δ (ppm) 160.73, 160.28, 151.72, 134.17, 127.66, 127.28, 122.69, 112.71, 55.96, 46.20, 44.69, 36.96, 29.18; MS (ESI) m/z 399 (M+H)$^+$.

Example 6

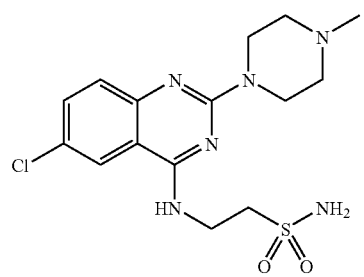 [SMILES: CN1CCN(c2nc(NCCS(N)(=O)=O)c3cc(Cl)ccc3n2)CC1]

2-(6-chloro-2-(4-methylpiperazin-1-yl)quinazoline-4-amino)-ethanesulfonamide

Prepared according to general method E from 2,4,6-trichloroquinazoline (200 mg) and 2-aminoethanesulfonamide hydrochloride (130 mg). Yield: 125 mg (38%). $^1$H-NMR (DMSO-d$_6$) δ (ppm) 8.23 (m, 1H), 8.04 (d, J=2.3 Hz, 1H), 7.51 (dd, J=2.3 Hz, J=8.9 Hz, 1H), 7.27 (d, J=8.9 Hz, 1H), 3.78 (m, 6H), 2.34 (m, 4H), 2.21 (s, 2H); $^{13}$C-NMR (DMSO-d$_6$) δ (ppm) 158.60, 158.27, 150.25, 132.45, 126.80, 123.86, 121.76, 110.95, 54.38, 52.49, 45.64, 43.09, 35.67; MS (ESI) m/z 461 (M+H)$^+$.

Example 7

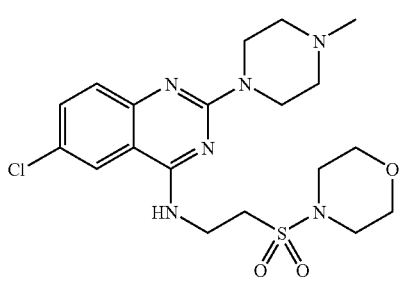 [SMILES: CN1CCN(c2nc(NCCS(=O)(=O)N3CCOCC3)c3cc(Cl)ccc3n2)CC1]

6-chloro-2-(4-methylpiperazin-1-yl)-N-(2-(morpholinosulfonyl)ethyl)quinazolin-4-amine Prepared according to general method E from 2,4,6-trichloroquinazoline (200 mg) and 4-(2-aminoethylsulfonyl)-morpholine hydrochloride (218 mg). Yield 303 mg (77%). $^1$H-NMR (CDCl$_3$) δ (ppm) 7.46 (s, 1H), 7.41-7.34 (m, 2H), 6.27 (m, 1H), 4.15-4.06 (m, 2H), 3.93 (t, J=4.4 Hz, 4H), 3.74 (t, J=4.7 Hz, 4H), 3.28-3.23 (m, 6H), 2.52 (t, J=5.0 Hz, 4H), 2.36 (s, 3H); $^{13}$C-NMR (CDCl$_3$) δ (ppm) 158.52, 158.31, 150.58, 133.27, 127.33, 126.05, 120.16, 110.72, 66.27, 54.84, 47.02, 45.91, 45.57, 43.46, 35.13.

Example 8

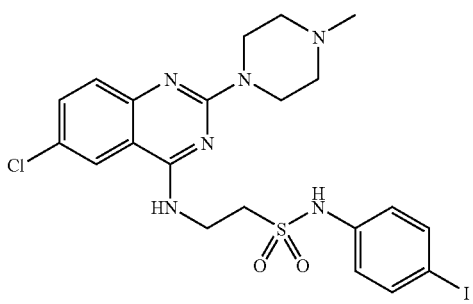 [SMILES: CN1CCN(c2nc(NCCS(=O)(=O)Nc3ccc(I)cc3)c3cc(Cl)ccc3n2)CC1]

2-(6-chloro-2-(4-methylpiperazin-1-yl)quinazoline-4-amino)-N-(4-iodophenyl)ethanesulfonamide Prepared according to general method E from 2,4,6-trichloroquinazoline (200 mg) and 2-aminoethane-N-(4-iodophenyl)sulfonamide (343 mg). Yield: 441 mg (87%). $^1$H-NMR (DMSO-$\delta_6$) δ (ppm) 9.69 (br s, 1H), 8.01-7.98 (m, 1H), 7.95 (d, J=2.4 Hz, 1H), 7.61-7.57 (m, 2H), 7.48 (dd, J=2.4 Hz, J=8.8 Hz, 1H), 7.27 (d, J=8.8 Hz, 1H), 7.04-7.01 (m, 2H), 3.85-3.80 (m, 2H), 3.69 (t, J=5.0 Hz, 4H), 3.53-3.50 (m, 2H), 2.31 (t, J=5.0 Hz, 4H), 2.24 (s, 3H); $^{13}$C-NMR (DMSO-$\delta_6$) δ 158.62, 158.01, 150.14, 137.77, 137.68, 132.51, 126.79, 123.94, 121.78, 120.89, 110.87, 87.49, 54.10, 48.71, 45.35, 42.77, 35.22.

Example 9

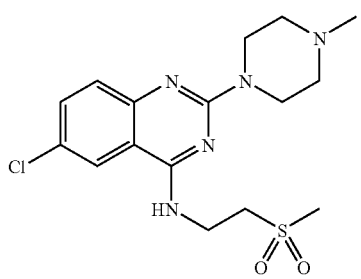 [SMILES: CN1CCN(c2nc(NCCS(C)(=O)=O)c3cc(Cl)ccc3n2)CC1]

2-(6-chloro-2-(4-methylpiperazin-1-yl)quinazoline-4-amino)-S-methylethanesulfone Prepared according to general method E from 2,4,6-trichloroquinazoline (200 mg) and commercially available 2-aminoethylmethylsulfone hydrochloride (151 mg). Yield 296 mg (90%). $^1$H-NMR (CDCl$_3$) δ (ppm) 7.45 (s, 1H), 7.41-7.32 (m, 2H), 6.25 (m, 1H), 4.13 (q, J=5.8 Hz, 2H), 3.88 (t, J=5.0 Hz, 4H), 3.43 (t, J=5.8 Hz, 2H), 2.96 (s, 3H), 2.46 (t, J=5.0 Hz, 4H), 2.32 (s, 3H); $^{13}$C-NMR (CDCl$_3$) δ (ppm) 158.61, 158.22, 150.30, 132.48, 126.83, 123.91, 121.75, 110.94, 54.38, 51.85, 45.65, 43.10, 34.34.

Example 10

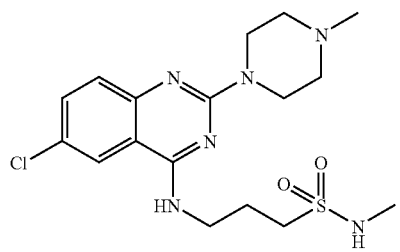 [SMILES: CNS(=O)(=O)CCCNc1nc(N2CCN(C)CC2)nc2ccc(Cl)cc12]

3-(6-chloro-2-(4-methylpiperazin-1-yl)quinazoline-4-amino)-N-methylpropanesulfonamide 2,4,6-Trichloroquinazoline (200 mg) was added to a solution of DIPEA (0.46 ml) and 3-aminopropane-N-methylsulfonamide hydrochloride (162 mg) in THF (3.0 ml) and the mixture was stirred overnight at room temperature. The solution was diluted with EtOAc and washed with water and brine. Drying over Na$_2$SO$_4$ and removal of the solvent gave a solid that was purified over SiO$_2$ (EtOAc: Hex, 1:1) to yield the 3-(2,6-dichloro-quinazoline-4-amino)-N-methylpropanesulfonamide intermediate. This intermediate was added to a microwave tube containing N-methylpiperazine (1.0 ml) and THF (3.0 ml) and this solution was heated at 130° C. After 15 minutes the obtained mixture was diluted with water and extracted with EtOAc. The combined organic extracts were dried over Na$_2$SO$_4$ and evaporated to give the crude product. Purification over SiO$_2$ (EtOAc:MeOH:Et$_3$N, 90:5:5) gave the title compound as a solid. Yield: 104 mg (30%). $^1$H-NMR (CDCl$_3$) δ (ppm) 7.48-7.32 (m, 3H), 5.91 (m, 1H), 5.91 (m, 1H), 3.88 (t, J=5.0 Hz, 4H), 3.78 (q, J=6.2 Hz, 2H), 3.12 (t, J=7.2 Hz, 2H), 2.78 (s, 3H), 2.45 (t, J=5.1 Hz, 4H), 2.32 (s, 3H), 2.22 (p, J=7.1 Hz, 2H). $^{13}$C-NMR (CDCl$_3$) δ (ppm); 158.88, 158.39, 150.28, 132.30, 126.76, 123.78, 121.81, 111.00, 54.39, 47.14, 45.64, 43.08, 28.34, 22.61; MS (ESI) m/z 413 (M+H)$^+$.

Example 11

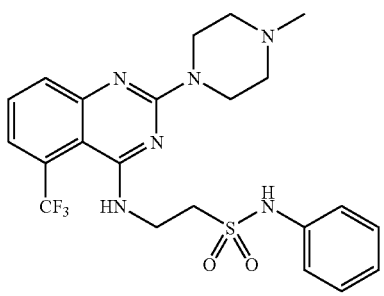 [SMILES: CN1CCN(c2nc(NCCS(=O)(=O)Nc3ccccc3)c3c(C(F)(F)F)cccc3n2)CC1]

2-(5-trifluoromethyl-2-(4-methylpiperazin-1-yl)quinazoline-4-amino)-N-phenylethanesulfonamide Prepared according to general method E from 2,4-dichloro-5-trifluoromethylquinazoline (200 mg) and 2-aminoethane-N-phenylsulfonamide (164 mg) Yield: 308 mg (93%). ¹H-NMR (DMSO-$\delta_6$) δ (ppm) 9.74 (br s, 1H), 7.64-7.57 (m, 2H), 7.50 (d, J=6.0 Hz, 1H), 7.32-7.28 (m, 2H), 7.24-7.21 (m, 2H), 7.11-7.06 (m, 1H), 6.56-6.55 (m, 1H), 3.98 (q, J=5.9 Hz, 2H), 3.74 (t, J=5.2 Hz, 4H), 3.47 (t, J=6.6 Hz, 2H), 2.32 (t, J=5.0 Hz, 4H), 2.23 (s, 3H).

Example 12

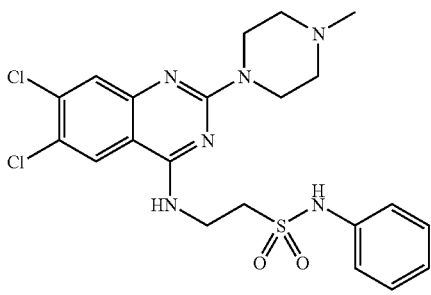 [SMILES: CN1CCN(c2nc(NCCS(=O)(=O)Nc3ccccc3)c3cc(Cl)c(Cl)cc3n2)CC1]

2-(6,7-dichloro-2-(4-methylpiperazin-1-yl)quinazoline-4-amino)-N-phenylethanesulfonamide Prepared according to general method E from 2,4,6,7-tetrachloroquinazoline (200 mg) and 2-aminoethane-N-phenylsulfonamide (164 mg). Yield: 284 mg (75%). ¹H-NMR (DMSO-$\delta_6$) δ (ppm) 8.15-8.13 (m, 2H), 7.42 (s, 1H), 7.30-7.26 (m, 2H), 7.23-7.20 (m, 2H), 7.09-7.06 (m, 1H), 3.86-3.81 (m, 2H), 3.71 (t, J=5.0 Hz, 4H), 3.50-3.47 (m, 2H), 2.31 (t, J=5.0 Hz, 4H), 2.22 (s, 3H); ¹³C-NMR (DMSO-$\delta_6$) δ (ppm) 158.44, 158.34, 151.12, 137.80, 134.90, 129.06, 125.57, 124.25, 123.60, 121.59, 119.08, 109.83, 54.23, 48.57, 45.58, 42.94, 35.23.

Example 13

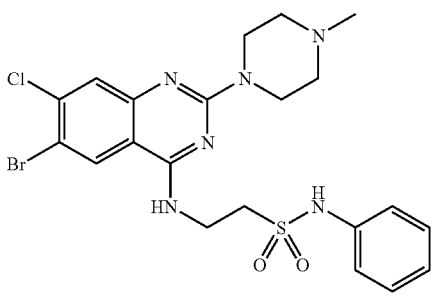 [SMILES: CN1CCN(c2nc(NCCS(=O)(=O)Nc3ccccc3)c3cc(Br)c(Cl)cc3n2)CC1]

2-(6-bromo-7-chloro-2-(4-methylpiperazin-1-yl)quinazoline-4-amino)-N-phenylethanesulfonamide Prepared according to general method E from 6-bromo-2,4,7-trichloroquinazoline (200 mg) and 2-aminoethane-N-phenylsulfonamide (140 mg) Yield: 208 mg (60%). ¹H-NMR (DMSO-$\delta_6$) δ (ppm) 9.68 (br s, 1H), 8.29 (s, 1H), 8.15 (m, 1H), 7.42 (s, 1H), 7.30-7.26 (m, 2H), 7.21 (d, J=7.2 Hz, 2H), 7.09-7.05 (m, 1H), 3.84-3.80 (m, 2H), 3.71 (t, J=5.2 Hz, 4H), 3.48 (t, J=7.2 Hz, 2H), 2.30 (t, J=4.6 Hz, 4H), 2.22 (s, 3H).

Example 14

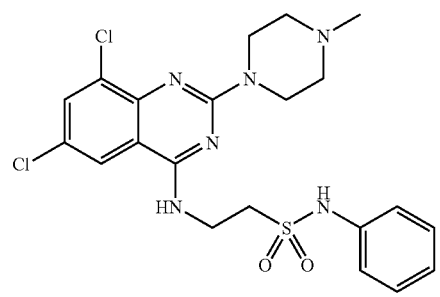 [SMILES: CN1CCN(c2nc(NCCS(=O)(=O)Nc3ccccc3)c3cc(Cl)cc(Cl)c3n2)CC1]

2-(6,7-dichloro-2-(4-methylpiperazin-1-yl)quinazoline-4-amino)-N-phenylethanesulfonamide 2,4,6,8-Tetrachloroquinazoline (200 mg) was added to a microwave tube containing EtOAc (3.0 ml) and DIPEA (0.27 ml). 2-aminoethane-N-phenylsulfonamide (164 mg) was added and the resulting mixture was stirred at r.t. until TLC indicated almost complete conversion of the starting material to the mono-substituted quinazoline. N-methylpiperazine (~1.0 ml) was added and the reaction mixture was heated at 120° C. for 10 minutes under microwave irradiation. The obtained mixture was then diluted with EtOAc and washed with water and brine. Drying of the organic phase with Na$_2$SO$_4$ and evaporation of the solvent gave the crude product that was purified over SiO$_2$ (gradient of 100% EtOAc-90% EtOAc, 5% Et$_3$N, 5% MeOH) to yield 305 mg (82% calculated over two steps) of the title compound as a solid. ¹H-NMR (DMSO-$\delta_6$) δ (ppm) 8.14 (t, J=5.2 Hz, 1H), 7.95 (d, J=2.4 Hz, 1H), 7.70 (d, J=2.4 Hz, 1H), 7.30-7.26 (m, 2H), 7.23-7.20 (m, 2H), 7.10-7.07 (m, 1H), 3.84-3.82 (m, 2H), 3.76 (t, J=5.0 Hz, 4H), 3.51-3.47 (m, 2H), 2.33 (t, J=5.0 Hz, 4H), 2.23 (s, 3H); ¹³C-NMR (DMSO-$\delta_6$) δ 158.75, 157.99, 146.96, 137.79, 131.76, 129.07, 123.61, 122.74, 121.05, 119.10, 111.55, 54.23, 48.56, 45.60, 42.93, 35.39.

Example 15

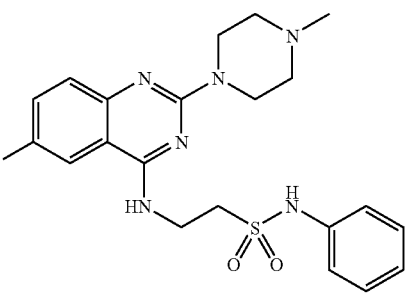

2-(6-iodo-2-(4-methylpiperazin-1-yl)quinazoline-4-amino)-N-phenylethanesulfonamide Prepared according to general method E from 2,4-dichloro-6-iodoquinazoline (200 mg) and 2-aminoethane-N- phenylsulfonamide (134 mg). Yield: 261 mg (76%). $^1$H-NMR (DMSO-$d_6$) δ (ppm) 9.93 (br s, 1H), 7.72 (dd, J=1.8 Hz, J=8.8 Hz, 1H), 7.34-7.18 (m, 3H), 7.12-7.03 (m, 2H), 3.77-3.66 (m, 6H), 3.50-3.43 (m, 2H), 2.27 (m, 4H), 2.20 (s, 3H).

Example 16

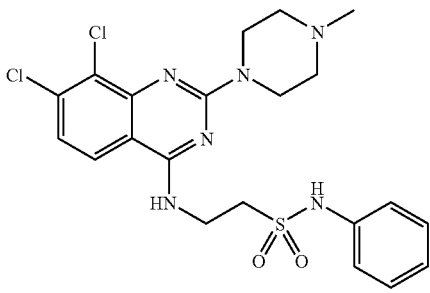 [SMILES: CN1CCN(c2nc(NCCS(=O)(=O)Nc3ccccc3)c3ccc(Cl)c(Cl)c3n2)CC1]

2-(7,8-dichloro-2-(4-methylpiperazin-1-yl)quinazoline-4-amino)-N-phenylethanesulfonamide Prepared according to general method E from 2,4,7,8-tetrachloroquinazoline (200 mg) and 2-aminoethane-N-phenylsulfonamide (164 mg). Yield: 306 mg (82%). $^1$H-NMR (DMSO-$d_6$) δ (ppm) 8.15 (m, 1H), 7.82 (d, J=8.8 Hz, 1H), 7.30-7.26 (m, 2H), 7.23-7.21 (m, 2H), 7.19 (d, J=8.8 Hz, 1H), 7.10-7.06 (m, 1H), 3.87-3.83 (m, 2H), 3.78 (t, J=5.0 Hz, 4H), 3.51-3.47 (m, 2H), 2.34 (t, J=5.0 Hz, 4H), 2.24 (s, 3H); $^{13}$C-NMR (DMSO-$d_6$) δ (ppm) 164.69, 163.67, 154.71, 143.09, 140.53, 134.35, 130.98, 128.88, 127.44, 125.76, 124.38, 114.86, 59.51, 53.93, 50.87, 48.21, 40.60.

Example 17

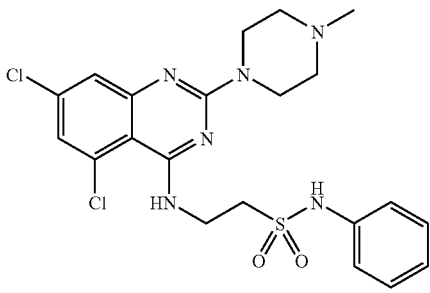 [SMILES: CN1CCN(c2nc(NCCS(=O)(=O)Nc3ccccc3)c3c(Cl)cc(Cl)cc3n2)CC1]

2-(5,7-dichloro-2-(4-methylpiperazin-1-yl)quinazoline-4-amino)-N-phenylethanesulfonamide Prepared according to general method E from 2,4,5,7-tetrachloroquinazoline (200 mg) and 2-aminoethane-N-phenylsulfonamide (164 mg). Yield: 296 mg (80%). $^1$H-NMR (CDCl$_3$) δ (ppm) 7.93 (m, 1H), 7.30-7.26 (m, 2H), 7.23-7.21 (m, 3H), 7.11 (d, J=2.1 Hz, 1H), 7.09-7.05 (m, 1H), 3.94 (q, J=6.4 Hz, 2H), 3.72 (t, J=5.0 Hz, 4H), 3.50 (t, J=6.8 Hz, 2H), 2.31 (t, J=5.0 Hz, 4H), 2.22 (s, 3H); $^{13}$C-NMR (CDCl$_3$) δ (ppm) 163.21, 162.74, 160.33, 143.13, 141.35, 135.00, 134.32, 128.78, 128.68, 127.10, 124.41, 111.74, 59.51, 53.95, 50.88, 48.17, 41.19.

Radioligand Displacement Studies at the Human H$_4$ Receptor

Cell culture and transfection. HEK 293T cells were maintained in Dulbecco's modified Eagle medium (DMEM) supplemented with 10% fetal bovine serum (FBS), 50 IU/ml penicillin, and 50 µg/ml streptomycin in 5% CO2 humidified atmosphere at 37° C. Approximately 4 million cells were seeded in a 10-cm dish and cultured overnight before transfection. For transfection of each dish of cells, the transfection mixture was prepared in 1 ml serum-free DMEM and contained 5 µg of human H$_4$R receptor plasmid and 15 µl of 1 mg/ml 25 kDa linear polyethyleneimine (Polyscience, Inc., USA). The mixture was incubated for 10-15 minutes at room temperature before it was added into the monolayer cell culture loaded with 5 ml fresh cell culture medium. Two days after transfection the cells were washed with PBS containing 1 mM EDTA, collected as pellet by centrifuging, and stored at −20° C. until use.

[$^3$H]Histamine Binding Assay.

For the radioligand binding study, pellets of transfected cells were homogenized in H$_4$R binding buffer (100 mM Tris-HCl, pH 7.4). The saturation binding assay was performed using different concentrations of [$^3$H]histamine (Perkin-Elmer Life Science, Inc., USA), while non-specific binding was determined by incubation in the presence of 3-10 µM of JNJ 7777120 in a total assay volume of 200 µl. For the displacement binding assay, the membranes were typically incubated with $10^{-4}$ to $10^{-11}$ M of ligands (stock concentration was 10 mM 1 DMSO) in the presence of [$^3$H]histamine in a total volume of 200 µl. The reaction mixtures were incubated for 1 hour at room temperature (22° C.), and harvested on 96-well glass fiber C plates that were pretreated with 0.3% 750 kDa PEI. The binding assay data were analyzed using Prism 4.0 (Graphpad Software Inc., USA).

Compounds of the invention showed activity in these assays.

The invention claimed is:

1. A compound of the formula

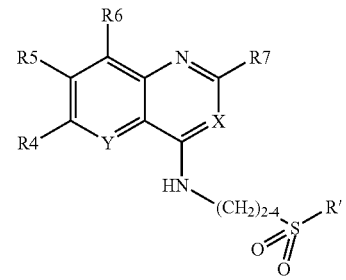

Wherein
X is N;
Y is CR$^3$;
R' is NR$^x$R$^y$ wherein R$^x$ and R$^y$ are each H, C$_1$-C$_6$ alkyl or phenyl, wherein phenyl is optionally substituted with halogen, or NR$^x$R$^y$ is a heterocyclic group that contains up to 6 C atoms and up to 3 heteroatoms selected from N, O, and S, which is saturated or partially or wholly unsaturated;
wherein R$^3$, R$^4$, R$^5$ and R$^6$ are independently selected from H, F, Cl, Br, I, C$_{1-4}$ alkyl, C$_{2-5}$ alkenyl, C$_{2-5}$ alkynyl, C$_{1-4}$ alkoxy, C$_{1-4}$ alkylthio, C$_{3-6}$ cycloalkyl, O—C$_{3-6}$ cycloalkyl, phenyl, benzyl, O-phenyl, NH-phenyl, S-phenyl, O—C$_{1-4}$ alkyl-phenyl, C$_{1-4}$ alkyl-phenyl, CF$_3$, O—CF$_3$, S—CF$_3$, hydroxy, nitro, cyano, O—C$_{1-4}$ alkyl-N(CH$_3$)$_2$, and NR$^a$R$^b$, wherein R$^a$ and R$^b$ are independently selected from H, C$_{1-4}$ alkyl, phenyl, benzyl and phenethyl, and wherein any phenyl, alkyl or cycloalkyl moiety is optionally substituted with 1 to 3 substituents selected from $C_{1-3}$ alkyl, halogen, hydroxy, amino and $C_{1-3}$ alkoxy;

wherein $R^7$ is selected from 4-7 membered heterocyclyl, $C_{3-7}$ cycloalkyl 4-7 membered heterocyclyl and bis-(4-7 membered heterocyclyl), and is optionally substituted with 1 to 3 substituents selected from $C_{1-3}$ alkyl, halogen, hydroxy, amino and $C_{1-3}$ alkoxy; or a pharmaceutically acceptable salt, ester or solvate thereof.

2. The compound according to claim 1, wherein three or all four of $R^3$, $R^4$, $R^5$ and $R^6$ are H.

3. The compound according to claim 1, wherein $R^7$ is 4-methylpiperazino.

4. The compound according to claim 1, wherein R' is $NH_2$.

5. The compound according to claim 1, selected from the group consisting of: 2-(6-chloro-2-(4-methylpiperazin-1-yl)quinazoline-4-amino)-N-methyl-N-phenylethanesulfonamide; 2-(6-chloro-2-(4-methylpiperazin-1-yl)quinazoline-4-amino)-N-phenylethanesulfonamide; 2-(6-chloro-2-(4-methylpiperazin-1-yl)quinazoline-4-amino)-N,N-diethylethanesulfonamide; 2-(6-chloro-2-(4-methylpiperazin-1-yl)quinazoline-4-amino)-N,N-dimethylethanesulfonamide; 2-(6-chloro-2-(4-methylpiperazin-1-yl)quinazoline-4-amino)-N-methylethanesulfonamide; 2-(6-chloro-2-(4-methylpiperazin-1-yl)quinazoline-4-amino)-ethanesulfonamide; 6-chloro-2-(4-methylpiperazin-1-yl)-N-(2-(morpholinosulfonyl)ethyl)quinazolin-4-amine; 2-(6-chloro-2-(4-methylpiperazin-1-yl)quinazoline-4-amino)-N-(4-iodophenyl)ethanesulfonamide; 3 (6 chloro-2-(4-methylpiperazin-1-yl)quinazoline-4-amino)-N-methylpropanesulfonamide; 2-(5-trifluoromethyl-2-(4-methylpiperazin-1-yl)quinazoline-4-amino)-N-phenylethanesulfonamide; 2-(6,7-dichloro-2-(4-methylpiperazin-1-yl)quinazoline-4-amino)-N-phenylethanesulfonamide; 2-(6-bromo-7-chloro-2-(4-methylpiperazin-1-yl)quinazoline-4-amino)-N-phenylethanesulfonamide; 2-(6,7-dichloro-2-(4-methylpiperazin-1-yl)quinazoline-4-amino)-N-phenylethanesulfonamide; 2-(6-iodo-2-(4-methylpiperazin-1-yl)quinazoline-4-amino)-N-phenylethane sulfonamide; 2-(7,8-dichloro-2-(4-methylpiperazin-1-yl)quinazoline-4-amino)-N-phenylethanesulfonamide; and 2-(5,7-dichloro-2-(4-methylpiperazin-1-yl)quinazoline-4-amino)-N-phenylethanesulfonamide.

6. A pharmaceutical composition comprising a compound according to claim 1, and at least one pharmaceutically acceptable additive.

* * * * *

UNITED STATES PATENT AND TRADEMARK OFFICE
CERTIFICATE OF CORRECTION

PATENT NO. : 8,530,486 B2
APPLICATION NO. : 12/811547
DATED : September 10, 2013
INVENTOR(S) : Smits et al.

It is certified that error appears in the above-identified patent and that said Letters Patent is hereby corrected as shown below:

In the Claims

Column 31, Claim 1
Line 6, "cycloalkyl 4-7" should read --cycloalkyl-4-7--.

Column 32, Claim 5
Line 6, "3 (6 chloro-" should read --3-(6-chloro- --.
Line 17, "phenylethane sulfonamide;" should read --phenylethanesulfonamide;--.

Signed and Sealed this
Nineteenth Day of November, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,530,486 B2  Page 1 of 1
APPLICATION NO. : 12/811547
DATED : September 10, 2013
INVENTOR(S) : Smits et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 232 days.

Signed and Sealed this
Fifteenth Day of September, 2015

Michelle K. Lee
*Director of the United States Patent and Trademark Office*